United States Patent

Chance et al.

4,055,720

Oct. 25, 1977

[54] DIAMINOTRIHALOPROPYL TRIAZINES: AND THEIR METHYLOL DERIVATIVES

[75] Inventors: Leon H. Chance, New Orleans; Judy D. Timpa, Metairie, both of La.

[73] Assignee: The United States of America, as represented by the Secretary of Agriculture, Washington, D.C.

[21] Appl. No.: 689,771

[22] Filed: May 25, 1976

[51] Int. Cl.$^2$ .......................................... C07D 251/48
[52] U.S. Cl. ........................................ 544/205; 560/226; 106/15 FP; 8/190; 252/8.8; 428/921
[58] Field of Search ...................................... 260/249.9

[56] References Cited

U.S. PATENT DOCUMENTS

| | | | |
|---|---|---|---|
| 3,162,633 | 12/1964 | Shaw | 260/249.9 |
| 3,536,710 | 10/1970 | Bartlett | 260/249.9 |

*Primary Examiner*—John M. Ford
*Attorney, Agent, or Firm*—M. Howard Silverstein; David G. McConnell; Salvador J. Cangemi

[57] ABSTRACT

2,4-Diamino-6(3,3,3-tribromo-1-propyl)-1,3,5-triazine and 2,4-diamino-6(3,3,3-trichloro-1-propyl)-1,3,5-triazine were prepared by the reaction of the corresponding methyl or ethyl γ-tribromo-butyrate or methyl or ethyl γ-trichlorobutyrate with biguanide. The N-methylol derivatives of the diaminotrihalopropyl triazines were prepared by the reaction of the triazines with aqueous formaldehyde. Two pure tetramethylol derivatives were prepared, namely: 2,4-bis[bis(hydroxymethyl)amino]-6-(3,3,3-tribromo-1-propyl)-1,3,5-triazine and 2,4-bis[bis(hydroxymethyl)amino]-6-(3,3,3-trichloro-1-propyl)-1,3,5-triazine. The tetramethylol derivatives were used to impart durable flame retardancy and wrinkle recovery to cellulosic textiles, particularly to cotton. Flame-retardancy was also imparted to wool and to blends of cotton and polyester.

4 Claims, No Drawings

DIAMINOTRIHALOPROPYL TRIAZINES: AND THEIR METHYLOL DERIVATIVES

FIELD OF THE INVENTION

This invention relates to diaminotrihalopropyl triazines, to the methylol derivatives thereof, to the the preparation thereof and to processes for imparting durable flame-retardancy and improved wrinkle recovery to cellulosic materials and protein fibers and blends of cotton and polyester fibers by treating said materials with the said methylol derivatives. More specifically, this invention relates to the synthesis of diaminotribromopropyl triazine, diaminotrichloropropyl triazine, and to the methylol derivatives of said triazines, useful in imparting durable flame-retardancy and wrinkle recovery to cellulosic and wool textiles and cotton-polyester textiles.

The main object of the instant invention is to provide a process for imparting to cotton and other cellulosic textiles improved flame retardancy which is durable to repeated laundering.

A second object of the instant invention is to provide a process for imparting to cellulosic and wool textiles improved wrinkle recovery in addition to the said flame-retardancy.

A third objective of the instant invention is to provide a new process for preparing essentially pure tetramethylol derivatives of diaminotrihalopropyl triazines.

A fourth objective of the instant invention is to disclose new methyl and ethyl γ-trihalobutyrates, useful in the preparation of diaminotrihalopropyl triazines.

A fifth objective of the instant invention is to disclose new diaminotrihalopropyl triazines and their tetramethylol derivatives, in which all three halogens are on the terminal carbon atom.

DESCRIPTION OF THE PRIOR ART

Searching the prior art we find that diaminohaloalkyl triazines have been prepared. For example, 2-(α-bromoethyl)-4,6-diamino-s-triazine has been prepared by the reaction of ethyl α-bromopropionate with biguanide [Overberger, C. G. and Michelatti, F. W. (J. Am. Chem. Soc. 80, 988-91 (1958)]. 2,4-Diamino-6dibromomethyl-s-triazine has been prepared by the reaction of 2,4,6-tris(tribromomethyl)-s-triazine with aqueous ammonia at room temperature. (Schaeffer, F. C. and Ross, J. H., J. Org. Chem. 29, 1527-1537 [1964]) Diaminohaloalkyltriazines have been prepared by others by the reaction of haloalkylnitriles with cyanoguanidine. For example, 2,4-diamino-6-(trichloromethyl)-1,3,5-triazine has been prepared by the reaction of trichloroacetonitrile with cyanoguanidine (Brit. patent specification No. 642,409, Sept. 6, 1950, to American Cyanamide Co., and Donald W. Kaiser. U.S. Pat. No. 3,330,830, July 11, 1967). No diaminotrihalopropyl-s-triazines are reported in which all three halogens are on the terminal carbon atom of the propyl group.

SUMMARY OF THE INVENTION

In the course of the investigation leading to the present invention, ethyl and methyl γ-trichlorobutyrates, and ethyl and methyl γ-tribromobutyrates of the formula $$X_3C-CH_2-CH_2-COOR \quad \text{(Formula I)}$$

where $X$ is chlorine or bromine and $R$ is ethyl or methyl, were prepared. The compounds of Formula I can be prepared by the reaction of water and the appropriate alcohol (ethyl alcohol or methyl) with γ-trichlorbutyronitrile or α-tribromobutyronitrile in the presence of an acid catalysts. While the compounds of Formula I are new compounds, this method of preparing them is well known. γ-Trichlorobutyronitrile and γ-tribromobutyronitrile can be prepared by the reaction of chloroform or bromoform with acrylonitrile essentially as reported by H. A. Bruson, et al., J. Am. Chem. Soc. 67, 601-602 (1945).

Further in the course of the investigation leading to the present invention it has been found that new compounds of the formula

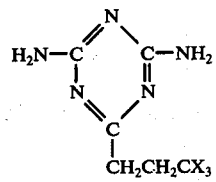

(Formula II)

where X is chlorine or bromine can be prepared by the reaction of biguanide with an ester of Formula I. Where X is chlorine the compound is called 2,4-diamino-6(3,3,3-trichloro-1-propyl)-1,3,5-triazine, and where X is bromine the compound is called 2,4-diamino-6(3,3,3-tribromo-1-propyl)-1,3,5-triazine. It has also found in the course of the investigation leading to the present invention that pure tetramethylol derivatives of the formula

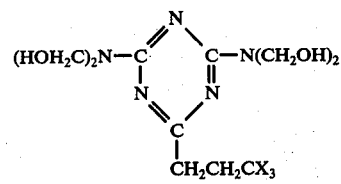

(Formula III)

where X is chlorine or bromine can be prepared by the reaction of compounds of Formula II with alkaline aqueous formaldehyde. The compounds of Formula III are new compounds. Where X is chlorine the tetramethylol derivative is called 2,4-bis[bis(hydroxymethyl)amino]-6(3,3,3-trichloro-1-propyl)-1,3,5-triazine, and where X is bromine it is called 2,4-bis[bis(hydroxymethyl)amino]-6-(3,3,3-tribromo-1-propyl)-1,3,5-triazine.

The compounds of Formula III are useful as flame-retardants for cellulosic textiles, particularly cotton and for wool and blends of cotton and polyester fibers. Said materials are made flame-retardant by (1) dissolving the tetramethylol derivative in an appropriate solvent, (2) impregnating the textile with the solution, (3) drying the textile, and (4) curing the textile at an elevated temperature.

The tetramethylol derivatives (compounds of Formula III) may also be applied to the particular substrate (cotton, ryaon, wool, paper, or cotton/polyester blends) in combination with organo-phosphorus compounds or certain metal oxides, such as antimony oxide, to enhance the flame-retardancy of the substrate. The flame-retardancy of cotton/polyester blends is particularly enhanced by the use of organophosphorus compounds or antiomony oxide.

Other compounds contemplated for use herein have the formula

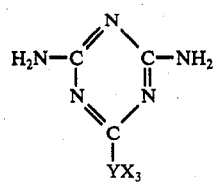

(Formula IV)

where Y is

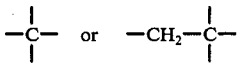

and X is chlorine or bromine. The methylol derivatives of compounds of Formula IV would be expected to be useful as flame-retardants in a manner similar to that described for compounds of Formula III.

PREFERRED EMBODIMENTS OF THE PREPARATION OF THE COMPOUNDS OF FORMULAS I, II, AND III

Ethyl and methyl γ-trichlorobutyrates and ethyl and methyl γ-tribromobutyrates were prepared by the reaction of water and the appropriate alcohol (ethyl alcohol or methyl alcohol) with γ-trichlorobutyronitrile or γ-tribromobutyronitrile in the presence of an acid catalyst. The preferred catalyst is dry hydrogen chloride gas. This method of preparing esters is well known.

The diaminohalopropyl triazines of Formula II were prepared by the reaction of biguanide with methyl or ethyl γ-trichlorobutyrate or methyl or ethyl γ-tribromobutyrate. The reaction is preferably carried out in methanol or ethanol solvent with stirring at room temperature until reaction is essentially complete. The preferred reaction temperature is 25°–35° C, and the preferred reaction time is 16–18 hours.

An alternative method for the preparation of diaminohaloalkyl triazines represented by Formula II involves the reaction of cyanoguanidine with haloalkylnitriles (Brit. patent specification No. 642,409, Sept. 6, 1950 and D. W. Kaiser. U.S. Pat. No. 3,330,830, July 11, 1967).

The tetramethylol derivatives of the diaminohalopropyl triazines are prepared by the reaction of the triazines of Formula II with alkaline aqueous formaldehyde. The reaction is preferably carried out by stirring the triazine in excess 35–38% aqueous formaldehyde at room temperatures ranging about from 25°–30° C for periods of time about from 15–22 hours to insure complete reaction. While the mole ratio of formaldehyde to diaminohalopropyl triazine is not critical it should be great enough such that a clear solution is formed. The ratio of formaldehyde to triazine may vary about from 14:1 to 24:1. The preferred ratio is about from 14:1 to 14.5:1. The pH of the solution should be alkaline and may vary about from 8–10. The preferred pH is about from 9.5–10.0. Although any suitable base may be used to adjust the pH of the reaction mixture, the preferred base is an alkali metal base such as sodium or potassium hydroxide. The crystalline tetramethylol derivatives of the diaminotriahlopropyl triazines are isolated by pouring the formaldehyde solution of the said derivatibe into water. The said derivative precipitates as a non-hygroscopic white crystalline compound because it is insoluble in water.

For convenience 2,4-diamino-6(3,3,3-tribromo-1-propyl)-1,3,5-triazine will be referred to hereinafter as DABT. The tetramethylol derivative of DABT will be referred to as TM-DABT. The chloro analog of DABT and TM-DABT will be referred to as DACPT and TM-DACPT, respectively.

TM-DABT and TM-DACPT can be applied to textiles from concentrated aqueous formaldehyde solutions or from any suitable organic solvents such as dimethylformamide (DMF) or dimethylacetamide (DMA). It is preferable, however, to apply TM-DABT or TM-DACPT to textiles from a combination of water and DMF or DMA. The amouunt of water in the DMF or DMA solutions may vary depending on the concentration of TM-DABT or TM-DACPT. The amount of water should not exceed that which would cause precipitation of the TM-DABT or TM-DACPT. The preferred concentration of TM-DABT or TM-DACPT used in the solutions, also referred to as pad-bath, depends on the type of textile being processed and on the degree of flame-retardancy desired.

Treatment of the textile materials may be carried out by impregnating the materials with a solution of the TM-DABT or TM-DACPT, drying, and curing at temperatures ranging about from 120° C to 160° C for periods of time about from 2 minutes to 10 minutes, the longer times being used with the lower temperatures. Since the rate of the reaction of the flame-retardant on the textiles is dependent on temperature, it is apparent to one skilled in the art that higher temperatures may be used. Also shorter heating times may be used depending on the type and effectiveness of the equipment used to cure the textiles. The preferred curing temperature for white textiles or textiles with a white background is 140°–145° C, because at higher curing temperatures there is a slight yellowing of the textiles.

Cotton textiles treated with TM-DABT by the processes of this invention have very good flame-retardancy which is durable to repeated launderings. In addition, the treated cotton textiles have improved wrinkle recovery, a good handle, and adequate strength retention. Strength properties may be improved by the addition of softening agents to the pad bath. A further advantage of the process is that the pad bath is quite stable. Satisfactory results were obtained on cotton fabric which was treated with solutions up to three weeks old.

The reaction of TM-DABT or TM-DACPT on cellulosic materials proceeds by both polymerization on the cellulosic fibrous substrate and crosslinking of the hydroxyl groups of cellulose molecules. The improved wrinkle recovery of cotton textiles, for example, is attributed to cross-linking of the cellulose molecules.

Other fibrous substrates which are made flame-retardant by this process are paper, rayon, wool and blends of cotton and polyester. Under certain conditions it may be advantageous to use phosphorus-containing compounds or certain metal oxides such as antimony oxides in combination with TM-DACPT or TM-DABT. For example, when olive drab cotton sateen (O.D. sateen) is treated with TM-DABT the fabric has a considerable afterglow when the flame is removed from a burning sample. In fact, untreated O.D. sateen has a considerable afterglow when ignited. The afterglow is attributed to the olive drab dye. The afterglow of TM-DABT treated O.D. sateen can be completely eliminated by treating the fabric with a very small amount of a phosphorus containing flame-retardant such as tetrakis (Hydroxymethyl) phosphonium hydroxide (THPOH) and ammonia. The flame retardancy of TM-DABT treated cotton-polyester textile can also be improved in the same way. The phosphorus flame-retardant may be incorporated in the TM-DABT pad bath or it may be applied to the fabric before treatment with TM-DABT or after treatment with TM-DABT. The preferred method using THPOH-ammonia is to apply the THPOH-ammonia to the fabric first and then apply the TM-DABT. In addition to phosphorus compounds, antimony oxides, such as $Sb_4O_6$, provide synergistic effects when used in combination with TM-DABT.

The durability of the TM-DABT flame-retardant to repeated laundering is attributed to its hydrolytic stability. This hydrolytic stability is attributed to the fact that all three bromine atoms are on the terminal carbon atom, and also to the fact that the —$CBr_3$ group is far enough removed from the triazine ring (by the distance of one —$CH_2$—$CH_2$— group) to be unaffected by the electron-withdrawing influence of the ring. In other words, the closer the —$CBr_3$ group is to the triazine ring the less stable the bromine atoms are to hydrolysis. Of course, the same thing applies to TM-DACPT. When all three halogen atoms are on the terminal carbon there is less opportunity for loss of halogen through dehydrohalogenation with an adjacent hydrogen atom.

TEXTILE TESTING

Textile materials which have been treated by the processes of this invention were tested by the following methods: wrinkle recovery (1a), flex abrasion resistance (1b), Elmendorf tearing strength (1c) and strip breaking strength (1d) were measured by standard ASTM procedures [(1) American Society for Testing Materials, 1968 Book of ASTM Standards, Part 24, Philadelphia, Pa.: (a) D1295-67, (b) D1175-64T, (c) 1424-63, (d) 168264)]. Stiffness was measured by the Tinius Olsen Test (Federal Test Method Standard No. 191, Method 5202, Dec. 31, 1968). Flame-retardancy was measured according to U.S. Department of Commerce, DOC FF 3-71 (as amended), Standard for the Flammability of Children's Sleepwear, Textile Chemist and Colorist 4(9), 71–76 (1972). In screening tests flame-retardancy of fabric samples was measured by the match test of W. A. Reeves, et al., Text. Research J. 23, 529 (1953). This method involves lighting the end of a strip of fabric 1 cm by 7 cm with the fabric surface vertical and determining the angular position, in degrees, at which it must be held for the flame to go out.

The following examples illustrate procedures that have been successfully used in carrying out the invention and are not meant as a limitation thereof.

PREPARATION OF NEW COMPOUNDS

EXAMPLE 1

Preparation of Ethyl γ-tribromobutyrate (Method 1)

γ-Tribromobutyronitrile (576.5 grams, 1.89 moles), water (34.52 grams, 1.92 moles), and 1000 ml of absolute ethanol were placed in a 2 liter flask equipped with a mechanical stirrer, a gas inlet tube, and a reflux condenser topped with a calcium sulfate drying tube. While stirring, dry hydrogen chloride gas was bubbled slowly into the mixture for about 50 minutes. The mixture became warm spontaneously. At this point HCl addition rate was increased to a rapid stream. After about 5 minutes all of the nitrile dissolved, the solution refluxed vigorously and $NH_4Cl$ began to precipitate. Rapid addition was continued for 10 minutes more and the HCl addition rate was reduced to a slow stream and continued for a total addition time of 2 hours. Stirring was continued for 2 hours more. Then the mixture was heated slowly on a water bath until reflux began. It was allowed to cool to room temperature. The $NH_4Cl$ was removed by filtration. The ethanol was removed on a rotary evaporation. The crude liquid ester remained as a residue containing a small amount of solid. The ester was dissolved in 300 ml of benzene and the resulting solution filtered to remove the solid. The benzene solution of the ester was shaken in a separatory funnel with 300 ml of water containing 10 gms of $Na_2CO_3$. The benzene layer was separated and dried over anhydrous $Na_2SO_4$. The benzene was removed by vacuum distillation leaving a 100% yield of crude ethyl α-tribromobutyrate. The crude ester was vacuum distilled; a yield of 98.6% of a clear colorless liquid was obtained, b.p. 73° C/0.13 mm. It had a pleasant odor characteristic of esters. Analysis: Calcd. for $C_6H_9Br_3O_2$ (percent): C, 20.42; H, 2.57; Br, 67.94. Found: C, 20.52; H, 2.57, Br, 68.03.

Method 2: Ethyl γ-tribromobutyrate was prepared essentially as in Method 1 except the HCl addition was begun at a rapid rate, in which case the γ-tribromobutyronitrile dissolved in 7 to 8 minutes and spontaneous reflux began in 10 to 15 minutes. The crude yield was 93%.

EXAMPLE 2

Preparation of Methyl γ-tribromobutyrate

The methyl ester was prepared by essentially the same method used in Example 1, Method 2, except that methanol was used instead of ethanol, and the mixture was refluxed 30 minutes after HCl addition was complete. A clear colorless liquid was obtained which distilled at 78° C/0.16 mm. The distillate crystallized to a white solid in a yield of 85.3% of pure methyl γ-tribromobutyrate, m.p. 39°–40° C.

Analysis: Calcd. for $C_5H_7Br_3O_2$ (percent): C, 17.72; H, 2.08; Br, 70.07. Found (percent): C, 17.72; H, 2.05; Br, 70.68.

EXAMPLE 3

Preparation of Ethyl γ-Trichlorobutyrate

Ethyl γ-trichlorobutyrate was prepared essentially by the method used in Example 1, Method 1, except that γ-trichlorobutyronitrile was used. A clear colorless liquid with a pleasant odor was obtained in a 90% yield, b.p. 74° C/0.13 mm.

Analysis: Calcd. for $C_6H_9Cl_3O_2$ (percent): C, 32.83; H, 4.13; Cl, 48.46. Found (percent): C, 32.68; H, 4.21; Br, 48.58.

EXAMPLE 4

Preparation of Methyl γ-Trichlorobutyrate

Methyl γ-trichlorobutyrate was prepared by the same method as that used for preparing methyl γ-tribromobutyrate (Example 2), except that γ-trichlorobutyronitrile was used. A clear colorless liquid was obtained in a 45.1% yield, which distilled at 57°–58° C/0.14 mm.

Analysis: Calcd. for $C_5H_7Cl_3O_2$ (percent): C, 29.23; H, 3.43; Cl, 51.76. Found (percent): C, 29.37; H, 3.43; Cl, 51.69.

EXAMPLE 5

Preparation of 2,4-Diamino-6(3,3,3-Tribromo-1-propyl)-1,3,5-Triazine (DABT)

Absolute methanol (1300 ml) was placed in a 3-neck flask equipped with a mechanical stirrer and a reflux condenser topped with a soda lime trap to exclude atmospheric $CO_2$. Metallic sodium (28.3 grams, 1.23 gram atoms) was added portion-wise in small pieces. This resulted in a methanolic solution of sodium methylate. (An alternative procedure would be to dissolve 1.23 moles of crystalline sodium methylate in the methanol.) Anhydrous biguanide sulfate (184.7 grams, 0.615 mole) was added to the solution. (The anhydrous biguanide sulfate was obtained by drying the dihydrate of biguanide sulfate to constant weight at 110° C.) The mixture was re-fluxed for 3 hours and then cooled to room temperature. The resulting solution contained the free base, biguanide, and sodium sulfate as a white precipitate. It was not necessary to filter off the $Na_2SO_4$ because it does not interfere with the next step. Crude ethyl α-tribromobutyrate (434.7 grams, 1.23 moles) was added in a slow stream, with stirring, over a period of about 20 minutes. Stirring was continued at room temperature for about 18 hours. The white precipitate, which contained both sodium sulfate and the DABT, was filtered. The filter cake was washed with 250 ml of fresh methanol and dried in an oven at 70°–85° C. In order to separate the DABT from the sodium sulfate, the precipitate was stirred with 725 ml of water, filtered, and the filter cake washed with 500 ml of water. Finally, the filter cake was washed with 125 ml of cold methanol and dried at 65° C. The DABT was a white powder, weighing 304.6 grams, a yield of 63.5%. The melting point was 170°–171° C, with decomposition.

The yield of DABT was no better when pure distilled ethyl γ-tribromobutyrate was used.

Analysis: Calcd. for $C_6H_8Br_3N_5$ (percent): C, 18.48; H, 2.07; Br, 61.49; N, 17.96. Found (percent): C, 18.26; H, 2.05; Br, 61.56; N, 18.02.

DABT was prepared in the same manner as described above except that methyl γ-trimbromobutyrate was used. A yield of 50.5% was obtained, which was significantly lower than when the ethyl ester was used.

EXAMPLE 6

Preparation of 2,4-Diamino-6(3,3,3-Trichloro-1-propyl)-1,3,5-Triazine (DACPT)

DACPT was prepared in exactly the same way as in Example 5 except that ethyl γ-trichlorobutyrate (21.95 grams 0.10 mole) was used. The yield was 15.82 grams, a 61.6% yield. This yield included a second crop of DACPT obtained by cooling the methanol filtrate to −20° C. The melting point was 187°–188° C with decomposition.

EXAMPLE 7

Preparation of 2,4-Bis[bis(hydroxymethyl)amino]-6(3,3,3-tribromo-1-propyl)-1,3,5-triazine, or tetramethylol 2,4-diamino-6(3,3,3-tribromo-1-propyl)-1,3,5-triazine (TM-DABT)

DABT (80.0 grams, 0.205 mole) and 37.3% aqueous formaldehyde (240.0 grams, 2.98 moles) were placed in a flask and adjusted to pH 10.0 by adding, with good stirring, 1.05 grams of 20% NaOH. The mixture was stirred at room temperature until a clear solution was obtained. For convenience, the mixture was stirred overnight for a total of about 20 hours. The solution was then added in a slow stream with stirring to 600 ml of water. The TM-DABT precipitated as a fine white powder. After standing for a while to allow complete precipitation, the white solid was collected on a filter. The TM-DABT was washed while on the filter with 175 ml of water. It was then air dried at room temperature. It weighed 97.2 grams, a 93% yield, m.p. 117°–118° C, dec.

Analysis: Calcd for $C_{10}H_{16}Br_3N_5O_4$ (percent): C, 23.55; H, 3.16; Br, 47.01; N, 13.73; formaldehyde, 23.55. Found (percent): C, 23.37; H, 3.04; Br, 46.92; N, 13.74; formaldehyde, 22.18.

EXAMPLE 8

Preparation of 2,4-Bis[bis(hydroxymethyl)amino]-6(3,3,3-Tribromo-1-Propyl)-1,3,5-Triazine or Tetramethylol 2,4-diamino-6(3,3,3-trichloro-1-propyl)-1,3,5-triazine (TM-DACPT)

DACPT (5.0 grams, 0.019 mole) and 37% aqueous formaldehyde (23.4 grams, 0.29 mole) were placed in a flask and with good stirring adjusted to pH 9.9 by adding 2 to 3 drops of 20% NaOH. After 2 hours stirring at room temperature the DACPT dissolved, forming a clear solution. The solution was allowed to stand overnight for a total reaction time of about 23 hours. The solution was poured, with stirring, into 50 ml of water at room temperature. A clear viscous liquid settled to the bottom of the beaker. The water was decanted from the viscous liquid, and 30 ml of fresh water was added. After stirring for a few minutes the viscous liquid crystallized to a fine white solid. The slurry of white crystals was cooled in an ice water bath and the crystals were filtered and washed on the filter with ice water. After air drying at room temperature, the crystals weighed 4.45 grams, a 60.6% yield, m.p. 100°–102° C.

Analysis: Calcd. for $C_{10}H_{16}Cl_3N_5O_4$ (percent): C, 31.89; H, 4.28; Cl, 28.24; N, 18.59; formaldehyde, 31.89. Found (percent): C, 31.74; H, 4.13; Cl, 28.39; N, 18.70; formaldehyde, 29.23.

APPLICATION OF COMPOUNDS OF THIS INVENTION TO TEXTILES

In all of the following examples the textile materials were treated with solutions of either TM-DABT or TM-DACPT. In some examples a phosphorus flame retardant was added to the solution. In other examples the phosphorus flame retardant was applied to the textile before treating with TM-DABT, and in other cases it was applied after treating with TM-DABT. The textiles were immersed in the solutions and the excess squeezed out through squeeze rolls. The wet pick-up depended on the squeeze roll pressure and the type of textile material. The fabrics were then dried and cured in a forced draft oven and finally rinsed in tap water and dried. Before textile tests were performed, the fabrics were given one process wash. This consisted of washing in a rotary-type washing machine with no detergent, followed by one tumble drying.

In one experiment the solvent for applying TM-DABT to the textile was 100% dimethylformamide (DMF). In other experiments the solvent was concentrated aqueous formaldehyde. In the preferred method a DMF/H₂O mixture was used as the solvent for the application of TM-DABT or TM-DACPT to textiles.

EXAMPLE 9

A solution of TM-DACPT was prepared by stirring 5.0 grams (0.19 mole) of DACPT with 23.4 grams of 37% formaldehyde adjusted to pH 9.9 with 20% NaOH until a clear solution was obtained. After standing about 18 hours methylolation was complete. To 22 grams of this TM-DACPT solution was added one drop of dilute hydrochloric acid to bring the pH of the solution to 6.8. Then 0.55 grams of 20% mixed catalyst (a 1:1 mole ratio of citric acid and MgCl₂.6H₂O). A sample of 4 ounce (oz) cotton flannelette impregnated with the solution (102% wet pick-up) was dried 5 minutes at 85° C and cured 5 minutes at 150° C, rinsed and dried. The fabric had a resin add-on of 21% and was only slightly flame-retardant. The match test angle was 0°.

EXAMPLE 10

A formaldehyde solution of TM-DABT was prepared essentially as in Example 7 except that it was not poured into water. Instead, the TM-DABT solution was diluted to a concentration of 25% by weight by adding additional 37% formaldehyde. The solution had a pH 9.5. Cotton flannelette samples (4 oz) impregnated with this solution were dried for 5 min. at 85° C and cured for 3 minutes at 130° C, 140° C, and 150° C, respectively. The resin add-ons were 14.2%, 19.7%, and 20.4%, respectively. The match test angles were 90°, 180°, and 180°, respectively. An angle of 180° indicates excellent flame-retardency.

EXAMPLE 11

Pure crystalline TM-DABT (4.0 grams) was dissolved in dimethylformamide (DMF). Cotton flannelette (4 oz) impregnated with this solution (110% wet pickup) was dried for 5 minutes at 85° C and cured for 5 minutes at 140° C, rinsed, and dried. The resin add-on to the fabric was 22.1%. The match test angle was 150°. After boiling for 4 hours in water containing 0.5% Na₃PO₄.12 H₂O and 0.1% wetting agent, the match test angle was 135°, indicating good durability to laundering.

Similar results were obtained when the solvent was dimethylacetamide.

EXAMPLE 12

The preferred solvent for treating textiles with TM-DABT is a DMF/H₂O mixture. A typical pad-bath is prepared as follows: Crystalline TM-DABT (75 grams) was dissolved in 171 grams of DMF (Reagent ACS grade). An alkylaryl polyether alcohol wetting agent (0.3 grams) was dissolved in 54 grams of distilled water and added with stirring to the DMF solution. The resulting solution contained 25% TM-DABT, 57% DMF, and 18% water by weight and had pH 5.0. The pH of the pad-bath varied about from 5.0 to 7.8 depending on the particular batch being prepared and the age of the solution. The solutions were quite stable and suitable for use for up to at least 3 weeks after preparation.

A typical procedure for treating fabric with the TM-DABT/DMF/H₂O solution described above consisted of padding the sample on a laboratory padder, drying the fabric and curing at specified temperatures, rinsing, and drying. The results on 4 oz cotton flannelette cured at various temperatures are shown in Table I. All samples were dried 5 minutes at 85° C.

TABLE I

| Add-on, % | Cured min./° C | Flame retardancy, match test angle, degrees |
|---|---|---|
| 20.0 | 10/120 | 180 |
| 19.5 | 3/130 | 180 |
| 20.9 | 3/140 | 180 |
| 20.8 | 5/140 | 180 |
| 19.2 | 3/150 | 180 |
| 20.1 | 2/160 | 180 |

All of the samples of cotton flannelette had very good flame-retardancy as shown by 180° match test angles.

A sample of 8.8 oz O.D. Cotton sateen was padded to a wet pickup of 74% with a solution containing 22% TM-DABT, 59% DMF, and 19% water. The sample was dried 5 minutes at 85° C and cured 5 minutes at 140° C, rinsed, and dried. It had an add-on of 11.3% and a match test angle of 180°.

EXAMPLE 13

Samples of cotton flannelette (4 oz) and cotton khaki twill (7.5 oz) were treated at constant dimensions on pin frames with TM-DABT by the method described in Example 12. The results are shown in Tables II, III, and IV.

TABLE II

| Fabric No. and type | Cured min./° C | Add-on % | DOC Char length, inches | Br % | N % |
|---|---|---|---|---|---|
| (1) Flannelette | 3/140 | 18.5 | 2.8 | 10.40 | 3.16 |
| (2) Flannelette | 3/140 | 14.2 | 4.4 | 9.22 | 2.54 |
| (3) Flannelette | 3/140 | 12.4 | 3.4 | 7.67 | 2.28 |
| (4) Twill | 5/140 | 11.1 | 1.6 | 6.38 | 2.02 |
| (5) Twill | 5/140 | 13.3 | 2.3 | 6.55 | 2.30 |

Samples (1), (4), and (5) in Table II were treated with solutions containing 25% TM-DABT, 57% DMF, and 18% water, sample (2) with solutions containing 20% TM-DABT, 60% DMF, and 20% water, and sample (3) with solutions containing 17% TM-DABT, 62% DMF, and 21% water. All solutions contained 0.1% wetting agent. All samples passed the DOC FF 3-71 flammability test. These results are after one process wash. Percent bromine and nitrogen on the fabric samples are shown.

TABLE III

RESULTS AFTER 50 LAUNDERINGS

| Fabric Sample No. | Add-on % | DOC Char length, inches | Br % | N % |
|---|---|---|---|---|
| (1) | 18.8 | 2.2 | 9.53 | 2.92 |
| (2) | 15.5 | 3.8 | 7.59 | 2.50 |
| (3) | 13.3 | 4.7 | 6.56 | 2.20 |
| (4) | 13.6 | 2.5 | 7.00 | 2.11 |
| (5) | 11.3 | 3.4 | 5.92 | 1.90 |

The data in Table III are the results of similar samples shown in Table II after 50 laundering cycles. All samples passed the DOC FF 3-71 flammability test.

TABLE IV

TEXTILE DATA AFTER ONE PROCESS WASH

| Fabric No. | Breaking strength lbs | Tear strength grams | Wrinkle recovery angle, degrees | Stiffness, bending moment, inch-lbs. × 10⁴ |
|---|---|---|---|---|
| (1) | 35.0 | 1040 | 270 | 4.3 |
| (2) | 33.1 | 1100 | 243 | 4.3 |
| (4) | 114.8 | 1800 | 216 | 21.3 |
| (5) | 165.8 | 1907 | 219 | 21.8 |

TABLE IV-continued
TEXTILE DATA AFTER ONE PROCESS WASH

| Fabric No. | Breaking strength lbs | Tear strength grams | Wrinkle recovery angle, degrees | Stiffness, bending moment, inch-lbs. $\times 10^4$ |
| --- | --- | --- | --- | --- |
| Control flannel | 32.4 | 1767 | 207 | 3.8 |
| Control twill | 170.4 | 3533 | 192 | 29.0 |

The data in Table IV shows strength, conditioned wrinkle recovery angles, and stiffness of treated fabric samples listed in Tables II and III. Data on untreated control fabrics are also shown. The fabrics all had a good hand when stiffness of the samples was compared to the controls. After sample (1) was laundered 50 times the breaking and tearing strengths were 24.4 lbs. and 900 grams, respectively. This compared favorably with a sample of untreated control flannelette which had been laundered 50 times. The breaking and tearing strength of the laundered control was 32.5 lbs. and 1040 grams, respectively.

White fabrics treated with TM-DABT are heat sensitive as evidenced by the fact that the fabrics yellow significantly when cured at temperatures of 150° C or more. White fabrics also yellow slightly after repeated laundering and tumble drying. The yellowing is less noticeable at the lower add-on of 11% to 15%.

EXAMPLE 14

A sample of O.D. sateen (8.8 oz) was treated with a solution containing 22% TM-DABT, 59% DMF, and 19% water. The sample was dried 5 minutes at 85° C and cured 5 minutes at 140° C. The sample had an add-on of 11.3% and had a match test angle for flame-retardancy of 180°. The fabric had an afterglow when ignited and the flame was extinguished. The untreated control also had a similar afterglow. This afterglow was due to the olive drab dye and not to the TM-DABT. This afterglow can be eliminated completely by treating the fabric with a phosphorus compound. For example, a 10% soltuion of tetrakis(hydroxymethyl)phosphonium hydroxide (THPOH) was prepared by dissolving tetrakis(hydroxymethyl)phosphonium chloride (Thpc) in water and adjusting to pH 7.5 with sodium hydroxide. The O.D. sateen fabric was padded with this solution, dried 3 minutes at 85° C, and exposed to ammonia gas in a chamber for a few minutes. The fabric was rinsed and dried. It contained 2.5% add-on of the THPOH flame retardant. This fabric sample was then further treated in the usual manner with TM-DABT. The sample had a 15.3% add-on of TM-DABT. It had excellent flame-retardancy and no afterglow.

EXAMPLE 15

TM-DABT and THPOH were also applied to cotton flannelette from a single bath. A solution of THPOH was prepared as in Example 14. Then a solution was prepared containing 20% TM-DABT, 5% THPOH, 57% DMF, and 18% water. A sample of cotton flannelette was padded with the solution, dried, and cured 3 minutes at 150° C. The fabric had a 20.8% add-on and had a match test angle of 135°.

EXAMPLE 16

A sample of cotton flannelette composed of a blend of 50% cotton and 50% polyester was treated with TM-DABT in the same manner as sample (1) in Example 13. The fabric had an add-on of 19.9%. Although it did not pass the DOC FF 3-71 flammability test it had reduced flammability as indicated by a match test angle of 90°.

A sample of the cotton/polyester flannelette with a 19.9% add-on of TM-DABT was further padded with a 20% solution of THPOH (prepared as in Example 14) to a wet pickup of about 90%. It was then dried 3 minutes at 85° C and finally exposed to ammonia gas in a chamber for 5 minutes. After rinsing and drying the fabric had an add-on of 12% of THPOH-$NH_3$ and a match test angle of 180°. Thus, the flame-retardancy of the cotton/polyester was improved considerably by adding a phosphorus compound.

Similar results were obtained when the THPOH-$NH_3$ was applied first, followed by TM-DABT. In fact, this method is preferred because a softer fabric is obtained.

EXAMPLE 17

Samples of rayon fabric, wool fabric, and filter paper were treated with TM-DABT in the same manner as sample (1) in Example 13. The resin add-ons were 14.7%, 24.8%, and 23.1%, respectively. The wool and paper had good flame-retardancy as indicated by a match test angle of 180° for each sample. The rayon had only fair flame-retardancy (match test angle of 90°).

We claim:
1. 2,4-Diamino-6(3,3,3-tribromo-1-propyl)-1,3,5-triazine.
2. 2,4-Diamino-6(3,3,3-trichloro-1-propyl)1,3,5-triazine.
3. 2,4-Bis[bis(hydroxymethyl)amino]-6(3,3,3-tribromo-1-propyl)-1,3,5-triazine.
4. 2,4-Bis[bis(hydroxymethyl)amino]-6(3,3,3-trichloro-1-propyl)-1,3,5-triazine.

* * * * *